(12) United States Patent
Arnoldy et al.

(10) Patent No.: US 6,187,962 B1
(45) Date of Patent: Feb. 13, 2001

(54) HYDROFORMYLATION PROCESS

(75) Inventors: Peter Arnoldy, Amsterdam (NL); Cornelis Mark Bolinger, Sugar Land, TX (US); Eit Drent, Amsterdam (NL); Johan Van Gogh, Amsterdam (NL); Cornelis Hyacinthus Maria Van Der Hulst, Amsterdam (NL); Robert Moene, Amsterdam (NL)

(73) Assignee: Shell Oil Company, Houston, TX (US)

( * ) Notice: Under 35 U.S.C. 154(b), the term of this patent shall be extended for 0 days.

(21) Appl. No.: 09/247,359

(22) Filed: Feb. 10, 1999

(30) Foreign Application Priority Data

Mar. 12, 1997 (EP) .................................................. 97300765

(51) Int. Cl.⁷ .................................................. C07C 45/50
(52) U.S. Cl. ........................................... 568/454; 568/451
(58) Field of Search ...................... 568/451, 454

(56) References Cited

FOREIGN PATENT DOCUMENTS 350922    1/1990  (EP) .
95/05354  2/1995  (WO) .

*Primary Examiner*—Sreeni Padmanabhan

(57) ABSTRACT

The invention relates to a hydroformylation process comprising the steps of:

Figure 1:
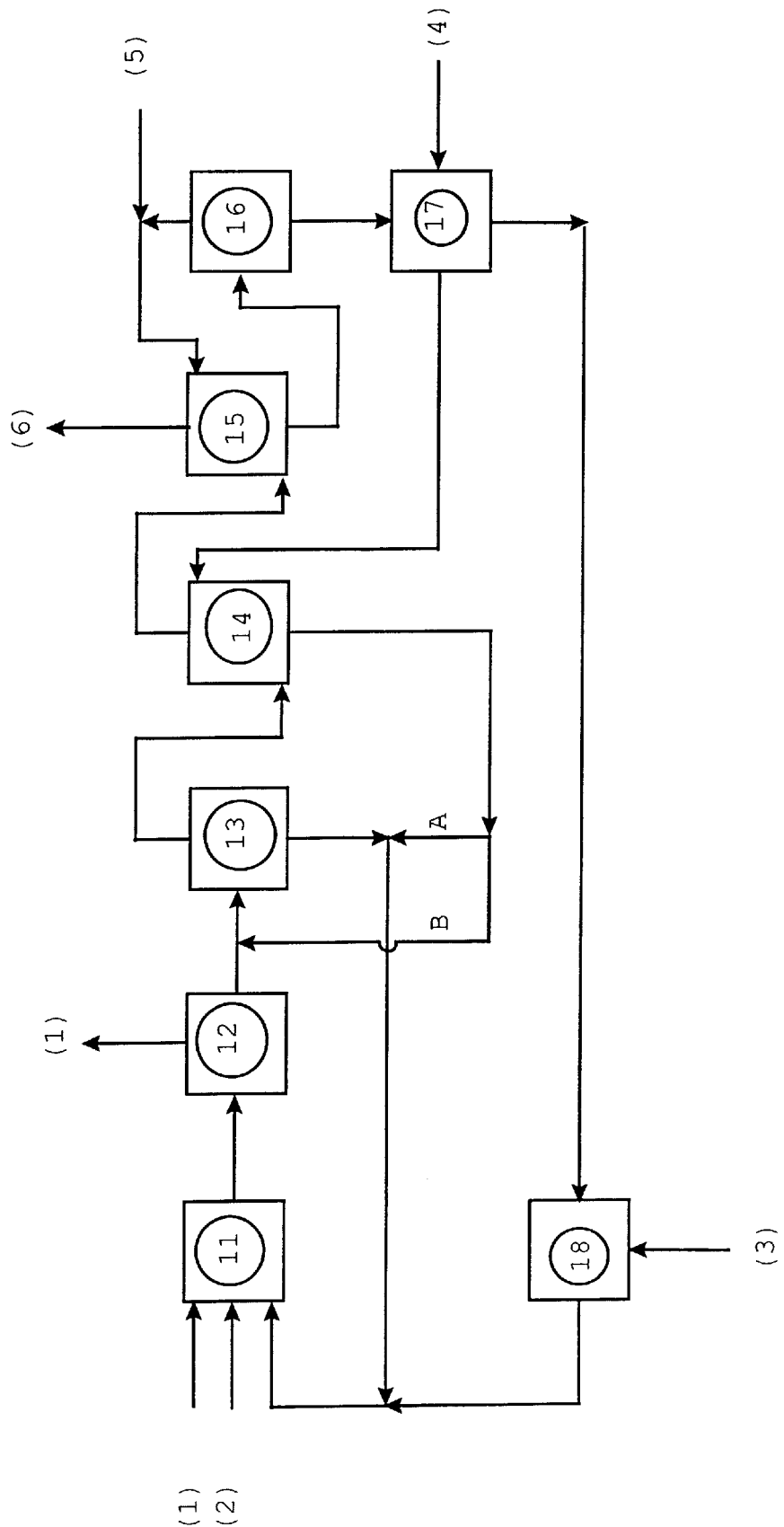

(a) contacting one or more ethylenically unsaturated compound(s) in a reaction zone with carbon monoxide and hydrogen gas in the presence of a solvent and a homogeneous catalyst based on a Group 8, 9 or 10 metal, and a non-ionically charged phosphorus ligand to form a crude hydroformylation product;

(b) allowing a major portion of the solvent, wherein a major portion of the catalyst is dissolved, to separate and be withdrawn from the crude hydroformylation product in a phase separation zone;

(c) removing from the separated hydroformylation product emerging from step (b) substantially all remaining catalyst dissolved therein with a non-aqueous extractant in an extraction zone.

11 Claims, 3 Drawing Sheets

HYDROFORMYLATION PROCESS

BACKGROUND OF THE INVENTION

The invention relates to a hydroformylation process wherein ethylenically unsaturated compounds are contacted with carbon monoxide and hydrogen gas in a reaction zone in the presence of a solvent and a homogeneous catalyst based on a Group 8, 9 or 10 metal (referring to the IUPAC classification of elements in use in 1997).

The hydroformylation of ethylenically unsaturated compounds, to form products such as aldehydes and/or alcohols, is of considerable industrial importance. As is apparent from the literature, e.g., "New Syntheses with Carbon Monoxide" by J. Falbe (Springer-Verlag 1980; ISBN 0-387-09674-4) and "Carbonylation" by H. M. Colqhoun, D. J. Thompson and M. V. Twigg (Plenum Press 1991; ISBN 0-306-43747-3) a multitude of catalysts based on Group 8, 9 or 10 metals (Fe, Ru, Os; Co, Rh, Ir; Ni, Pd, and Pt) have been used in hydro-formylation processes. The most important industrial hydroformylation processes are presently based on the Group 9 metals; Co and Rh. Extensive patent art is also present on hydroformylation processes based on the Group 10 metals, Ni, Pd and Pt.

For various reasons, not in the least the costs of replacing lost catalyst, the catalyst must be recovered from the hydroformylation product. Mere distillation of the hydroformylation product, however, may inactivate and hence destroy the catalyst. Catalysts that are prone to destruction are therefore separated, for instance, by extraction.

In International application WO 95/05354 a process is disclosed wherein a major portion of the metal component of the catalyst system is recovered by causing at the end of the reaction the crude product to form two immiscible layers, and separating the layer comprising the hydroformylation product from the layer comprising the catalyst. The product layer, however, will still contain active catalyst. This reference provides no teaching how that should be recovered.

From EP-A-0,350,922 a process is known for the separation and recovery of an aldehyde product from a non-aqueous hydroformylation reaction product composition. The process involves phase separation using added water or both added water and an added non-polar hydrocarbon compound. Comparative example 1 of this reference illustrates the inadequacy of recovery by mere phase separation, whilst improved phase separation is shown when water is added. However, it should be observed that this process is conducted in the presence of a water soluble hydroformylation catalyst system. Thus, ionically charged phosphorus ligands are used, which will together with the metal complex- easily separate into the aqueous phase during the phase separation step. For catalyst systems based on non-ionically charged phosphorus ligands, which are the more common type ligands, this document provides no teaching either.

The inventors have set out to develop a hydro-formylation process, based on non-ionically charged ligands, with essentially full catalyst recovery.

SUMMARY OF THE INVENTION

Accordingly, a hydroformylation process is provided comprising the steps of:
(a) contacting one or more ethylenically unsaturated compoundts) with carbon monoxide and hydrogen gas in a reaction zone in the presence of a solvent and a homogeneous catalyst based on a Group 8, 9 or 10 metal and a non-ionically charged ligand, to form a crude reaction product;
(b) allowing a major portion of the solvent, wherein a major portion of the catalyst is dissolved, to separate and be withdrawn from the crude hydroformylation product in a phase separation zone; and
(c) removing from the separated hydroformylation product emerging from step (b) substantially all remaining catalyst dissolved therein with a non-aqueous extractant in an extraction zone.

In step (c) as extractant preferably the same substance is used as the solvent used in step (a), thereby avoiding contamination of recycle streams.

In a (fully integrated) process that uses recycle streams, the extraction step (c) is preferably carried out (in a multi-stage mode) with an amount of extractant that matches the amount of solvent that is dissolved in the hydroformylation product emerging from step (c). Note that after the separation step (b) the hydroformylation product is still saturated with solvent. For instance, at a temperature of 40° C., 100 g of a sulfolane-saturated crude $C_{11}$–$C_{12}$ olefin-derived hydroformylation product will contain about 8 g of sulfolane and therefore about 8 g of sulfolane is to be used for extraction. Obviously, the amount of extractant need not be an exact match; the process may be adapted to cope with for instance 0.9 to 1.1 times that amount.

Extraction step (c) affords a catalyst-loaded extractant. When extractant from step (c) and solvent are of the same substance, the catalyst-loaded extractant may be led to the reaction zone of step (a) and/or to the separation zone of step (b). The inventors found the latter embodiment to be beneficial as thereby substantially higher separation efficiencies could be realised in step (b).

The solvent-extracted hydroformylation product emerging from step (c) will contain solvent and/or extractant. Typically, the solvent and/or the extractant also needs removal. Distillation is one option, as the extracted hydroformylation product is now freed from valuable catalyst. However, this manner of separation may be less applicable when the solvent, the extractant and the product have similar boiling points. Therefore, removal by washing is preferred.

DETAILED DESCRIPTION OF THE INVENTION

Obviously, in case the solvent and/or the extractant are removed by washing, the problem should not be augmented by the presence of the medium used for washing. In other words, the solubility of the hydro-formylation product into. the medium should be less than into the solvent and/or extractant. Furthermore, the washing medium should preferably be a harmless impurity without undesired side-effects when becoming part of the recycle streams. Moreover, the medium should be cheap.

Water was found to be quite effective as washing medium. Thus, a step (d) is preferably added to the process of the invention that comprises:
(d) removing from the extracted hydroformylation product emerging from step (c) substantially all remaining solvent and/or extractant dissolved therein with a washing medium, that is preferably water, in a washing zone, separating the solvent and/or extractant from the washing medium emerging from the washing zone and optionally reusing each.

Preferably the water-washing is conducted (in a multi-stage mode) at temperatures in excess of 60° C., more preferably in excess of 70° C. and at a phase ratio of crude versus medium varying from 1:0.2 to 1:1 w/w. The lower temperature is important to avoid emulsification.

In the preferred embodiment, wherein the extractant and the solvent are of the same substance, the isolated extractant is preferably reused as extractant in step (c). Surprisingly, this small amount of extractant is sufficient to effectively remove substantially all the remaining catalyst from the separated hydro-formylation product emerging from step (b).

The extraction may be conducted in a column equipped with a rotary-disk contactor (cf. Perry's Chemical Engineers' Handbook, 6th ed., p. 21–77 and further) or a packed bed column. The packed bed column is more efficient in the present process, avoiding undesired emulsification, and is hence preferred. Highest extraction efficiencies may be realised using a packed bed column with structured packing.

The separated solvent emerging from step (b) contains valuable catalyst and is therefore preferably fed to the reaction zone of step (a) of the process.

Preferably, the phase separation of step (b) is caused by cooling the (single-phase) hydroformylation product to a temperature within the range of 0 to 80° C., more preferably within the range of 15 to 60° C. However, it is within the reach of those skilled in the art to establish in each case the degree of cooling and the optimal amount of solvent required for phase separation to occur. No specific pressure requirements apply. The experimental results provided hereinafter are also indicative for the amount of solvent preferably to be used.

A further embodiment of the process of the invention relates to phase separation problems. These problems concern the excessively long time required for the layers to separate cleanly and the need for a coolant having a temperature below room temperature in case of phase separation at ambient temperature. The former problem appears due to the formation of a fine emulsion, the latter to the relationship between temperature and the catalyst distribution over both layers. Note that the second problem has already been partly addressed by the process of the invention as the catalyst dissolved in the product layer is recovered by extraction.

The inventors found that use of a centrifuge, a filterbed coalescer or an electrostatic coalescer in step (b) of the process will break the emulsion in a highly expedient manner without loss of valuable material. On the other hand, the use of conventional equipment such as an open settler, a parallel-plate settler and a hydrocyclone have proved to be less successful (for definitions on equipment to break emulsions cf. "Perry's Chemical Engineers' Handbook", 6th ed., pp. 21–64; 21–65 and 21–66).

As in EP-A-0,350,922, it has been found helpful to add liquid saturated hydrocarbons to the crude hydroformylation product before phase separation. Preferably, these hydrocarbons have boiling points equal to or less than the light ends (i.e., paraffin byproducts produced in the process). Indeed, the light ends themselves may be used. Benefits include accelerated phase separation, even at higher temperatures. This allows for use of less cold and hence less expensive coolants. Further benefits include improved extraction (as the catalyst is typically less soluble in saturated hydrocarbons) and washing of the extracted hydroformylation product. Conveniently these hydro-carbons are used in an amount of 10 to 50 percent by weight based on the product stream.

In addition to the main process as described above, it was found beneficial to recycle a portion of the hydroformylation product to the reaction zone, to improve the dissolution of the ethylenically unsaturated compounds in the solvent. This is particularly advantageous during start-up. Conveniently, up to 20 per cent of the hydroformylation product may so be recycled.

The ethylenically unsaturated compounds used as starting material may be compounds having a single double bond. They may bear functional groups attached to their backbone or have non-carbon atoms in their backbone. Preferably, they have from 2 to 30 carbon atoms per molecule. They may also be applied as a mixture of such ethylenically unsaturated compounds. More preferably, the ethylenically unsaturated compound is an olefin having from 4 to 24 carbon atoms per molecule, or it is a mixture of such olefins. It is believed that with olefins having only 2 or 3 carbon atoms per molecule it may be difficult to cause phase separation in step (b) to occur. Most preferred are olefins having from 6 to 18 carbon atoms, or mixtures thereof. Such olefin mixtures are commercially readily available and their products represent valuable detergent and plasticizer intermediates.

Carbon monoxide and hydrogen gas may be supplied in equimolar or non-equimolar ratios, e.g. in a ratio within the range of 5:1 to 1:5. Preferably they are supplied in a ratio within the range of 2:1 to 1:2.5.

The hydroformylation can be suitably carried out at moderate reaction conditions. Hence temperatures in the range of 50 to 200° C. are recommended, preferred temperatures being in the range of 70 to 160° C. Reaction pressures in the range of 1 to 300 bar absolute are suitable, but in the range of 5 to 100 bar abs are preferred. Lower or higher pressures may be selected, but are not considered particularly advantageous.

Suitable solvents that are capable of selectively dissolving substantially all of the catalyst system from the hydroformylation product, are usually characterized by the presence of an aprotic, polar group in the molecule. Solvents containing strong polar groups are in particular preferred if the unsaturated starting material has a relatively low molecular weight, e.g., if ethylenically unsaturated compounds having from 5 to 7 carbon atoms are used. For the hydroformylation of higher molecular weight unsaturated compounds, e.g. olefins having from 12 to 16 carbon atoms the use of less polar solvents will usually be satisfactory.

Solvents comprising or substantially consisting of sulphones are preferred. Solvents that are particularly preferred comprise dialkylsulphones such as dimethyl-sulphone and diethylsulphone; and cyclic sulphones such as sulfolane (tetrahydrothiophene-2,2-dioxide), 2-methylsulfolane and 2-methyl-4-ethylsulfolane. A further class of suitable solvents includes the class of compounds having 2 or more cyano groups, such as malononitrile, succinonitrile, adiponitrile, dihydro-muconitrile, pimelonitrile, suberonitrile, 1,6-di-cyanocyclohexane, 1,2,4-tricyanobutane, etc., and mixtures thereof either or not with sulfolane.

Other mixtures of solvents may also be used, for example a mixture of a sulphone and/or a compound having 2 or more cyano groups with a protic solvent, such as an alcohol. In the hydroformylation of olefins, typically an alcohol is selected which is identical or similar to the alcohol obtained in the hydroformylation reaction. Sulfolane is the preferred solvent for the present process.

The extractant is characterized by the presence of an aprotic, polar group in the molecule as well. The compounds mentioned above (as solvent) are therefore suitable extractants. In line with the preferred embodiment, the extractant and solvent are the same.

The amount of solvent to be used in the process of the invention may vary considerably. For instance, the amount of solvent may vary from 3 to 50 percent by volume of the volume of the reaction mixture comprising solvent, ethylenically unsaturated compound(s) and catalyst.

In the present specification the catalyst may be an unmodified Group 8, 9 or 10 metal carbonyl and Group 8, 9 or 10 metal carbonyl hydride, but more preferably the catalyst is modified with one or more noncarbonyl ligands. Examples of noncarbonyl ligands that already find employ in the manufacture of hydroformylation products include phosphines, phosphine oxides, phosphites and the like. The present invention is particularly useful when employing a modified, Group 8, 9 or 10 metal based catalyst, more in particular based on Co, Rh, Ni, Pd or Pt. The invention is particularly useful when employing any of the catalysts described in EP-A-0,220,767, U.S. Pat. No. 3,527,818, EP-A-0,495,547 and especially when applying the catalysts of WO 95/05354, all incorporated by reference.

A suitable catalyst system, for instance, comprises
(i) a source of group 10 metal cations;
(ii) a source of anions, other than halide anions, e.g., derived from acids having a pKa value of less than 3 when measured in an aqueous solution at 18° C.; and
(iii) a source of bidentate ligands of the formula

$$R^1R^2P\text{-}R\text{-}PR^3R^4 \qquad (I)$$

wherein R is a bivalent bridging group containing from 1 to 10 atoms in the bridge and $R^1$, $R^2$, $R^3$ and $R^4$ independently represent substituted or non-substituted aliphatic groups, or $R^1$ together with $R^2$ and/or $R^3$ together with $R^4$ represent a bivalent group with at least 5 ring atoms whereby the two free valencies are linked to the phosphorus atom.

Examples of suitable metal sources are palladium(II) acetate and platinum(II) acetylacetonate.

As anion source, other than halide anions, any compound generating anions may be used. Such compounds may comprise acids or salts thereof; for example, any of the acids mentioned above, which may also participate in the salts of the group 8, 9 Or 10 metals. The anions are preferably derived from strong acids, i.e., acids having a pKa value of less than 3, preferably less than 2 as measured in aqueous solution at 18° C. The anions derived from these acids are non-coordinating or weakly coordinating with the metals. The stronger the acid, the less the anion coordinates with the metal cation and the higher is the linearity of the hydroformylation product.

Typical examples of suitable anions are anions of phosphoric acid, sulphuric acid, sulfonic acids and halogenated carboxylic acids such as trifluoroacetic acid. Also, complex anions are suitable, such as the anions generated by a combination of a Lewis acid such as $BF_3$, $B(C_6F_5)_3$, $AlCl_3$, $SnF_2$, $Sn(CF_3SO_3)_2$, $SnCl_2$ or $GeCl_2$, with a protic acid, such as a sulfonic acid, e.g. $CF_3SQ_3H$ or $CH_3SO_3H$ or a hydrohalogenic acid such as HF of HCl, or a combination of a Lewis acid with an alcohol. Examples of such complex anions are $BF_4^-$, $SnCl_3^-$, $[SnCl_2.CF_3SO_3]^-$ and $PF_6^-$. The preferred anion source is trifluoromethanesulfonic acid.

The bridging group in the diphosphine, represented by R, typically is composed of carbon atoms. Preferably the bridging group contains two or three carbon atoms in the bridge.

In the ligands of formula (I), $R^1$, $R^2$, $R^3$ and $R^4$ may independently represent various non-cyclic or cyclic groups, optionally substituted with substituents such as alkoxy groups with 1 to 4 carbon atoms, halogen atoms or ($C_1$ to $C_4$ alkyl)amino groups. Examples are alkyl groups such as ethyl, isopropyl, sec-butyl and tert-butyl groups, cycloalkyl groups such as cyclo-pentyl and cyclohexyl groups, aryl groups such as phenyl and tolyl groups.

However, preferably at least one of $R^1$ together with $R^2$ or $R^3$ together with $R^4$ represents a bivalent (substituted) group.

The bivalent (substituted) group preferably contains from 6 to 9 atoms in the ring. More preferably it is a cyclic group containing 8 ring atoms. Substituents, if any, are usually alkyl groups having from 1 to 4 carbon atoms. As a rule, all ring atoms are carbon atoms, but bivalent cyclic groups containing one or two heteroatoms in the ring, such as oxygen or nitrogen atoms are not precluded. Examples of suitable bivalent cyclic groups are 1,4-cyclohexylene, 1,4-cycloheptylene, 1,4-cyclooctylene, 1,5-cyclo-octylene, 2-methyl-1,5-cyclooctylene, 2,6-dimethyl-1,4-cyclooctylene and 2,6-dimethyl-1,5-cyclooctylene groups.

Preferred bivalent cyclic groups are selected from 1,4-cyclooctylene, 1,5-cyclooctylene, and methyl (di)substituted derivatives thereof.

Mixtures of ligands comprising different bivalent cyclic groups may be used as well, e.g. mixtures of ligands with 1,4-cyclooctylene and ligands with 1,5-cyclooctylene groups. Preferred bidentate ligands of formula (I) are therefore 1,2-bis(1,4-cyclo-octylenephosphino)ethane, 1,2-bis(1,5-cyclooctylene-phosphino)ethane and mixtures thereof and 1,3-bis(1,4-cyclooctylenephosphino)propane, 1,3-bis(1,5-cyclo-octylenephosphino)propane and mixtures thereof.

For the preparation of the bidentate ligands, reference is made to known techniques, for example the method disclosed in GB-A-1,127,965.

The quantity in which the catalyst system is used, is not critical and may vary within wide limits. Usually amounts in the range of $10^{-8}$ to $10^1$, preferably in the range of $10^{-7}$ to $10^{-2}$ mole atom of metal per mole of ethylenically unsaturated compound are used. The amounts of the participants in the catalyst system are conveniently selected such that per mole atom of metal from 0.5 to 10, preferably from 1 to 6 moles of bidentate ligand are used, from 0.5 to 15, preferably from 1 to 8 moles of anion source or a complex anion source.

A preferred feature of the process of the invention consists in the presence of a catalyst promoter, comprising a source of halide anions (Cl, Br or I anions), with the proviso that the molar ratio between halide anions and the metal cations should be at most 5:1. Preferably, the molar ratio between halide anions and metal cations is at most 1:1, for instance from 0.02:1 to 1:1.

As source of halide anions any compound generating halide anions under the reaction conditions may be used.

Recommended are inorganic compounds such as hydrogen halides, e.g. HCl, HBr and HI and metal halides, e.g. NaCl, $MgBr_2$, $ZnCl_2$, $ZnI_2$, KBr, RbCl, CsCl, CsI, $MgI_2$ and CuCl. Catalyst promoters comprising a source of chloride anions are in particular preferred.

FIGURES

Figure 2:
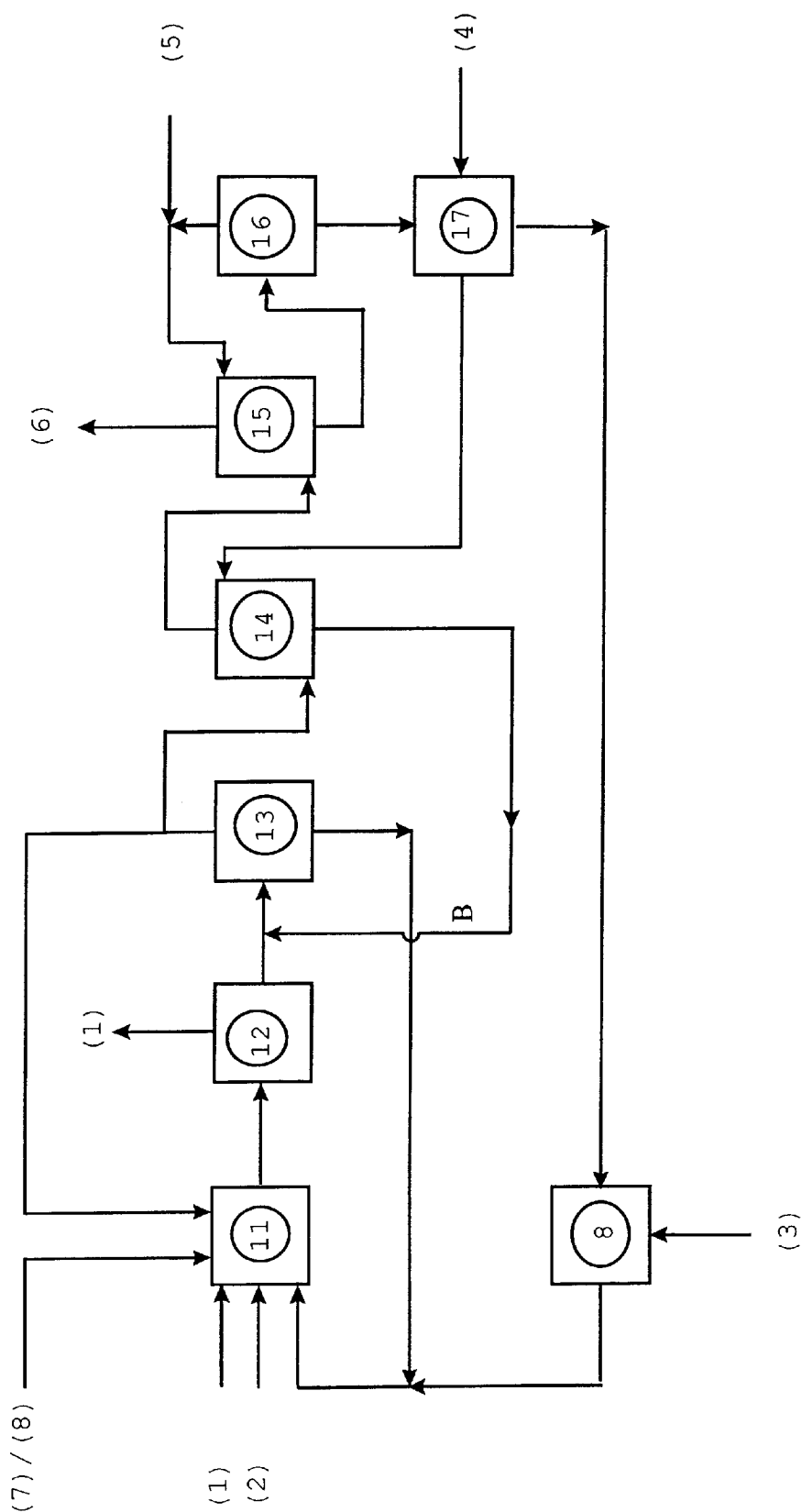
Figure 3:
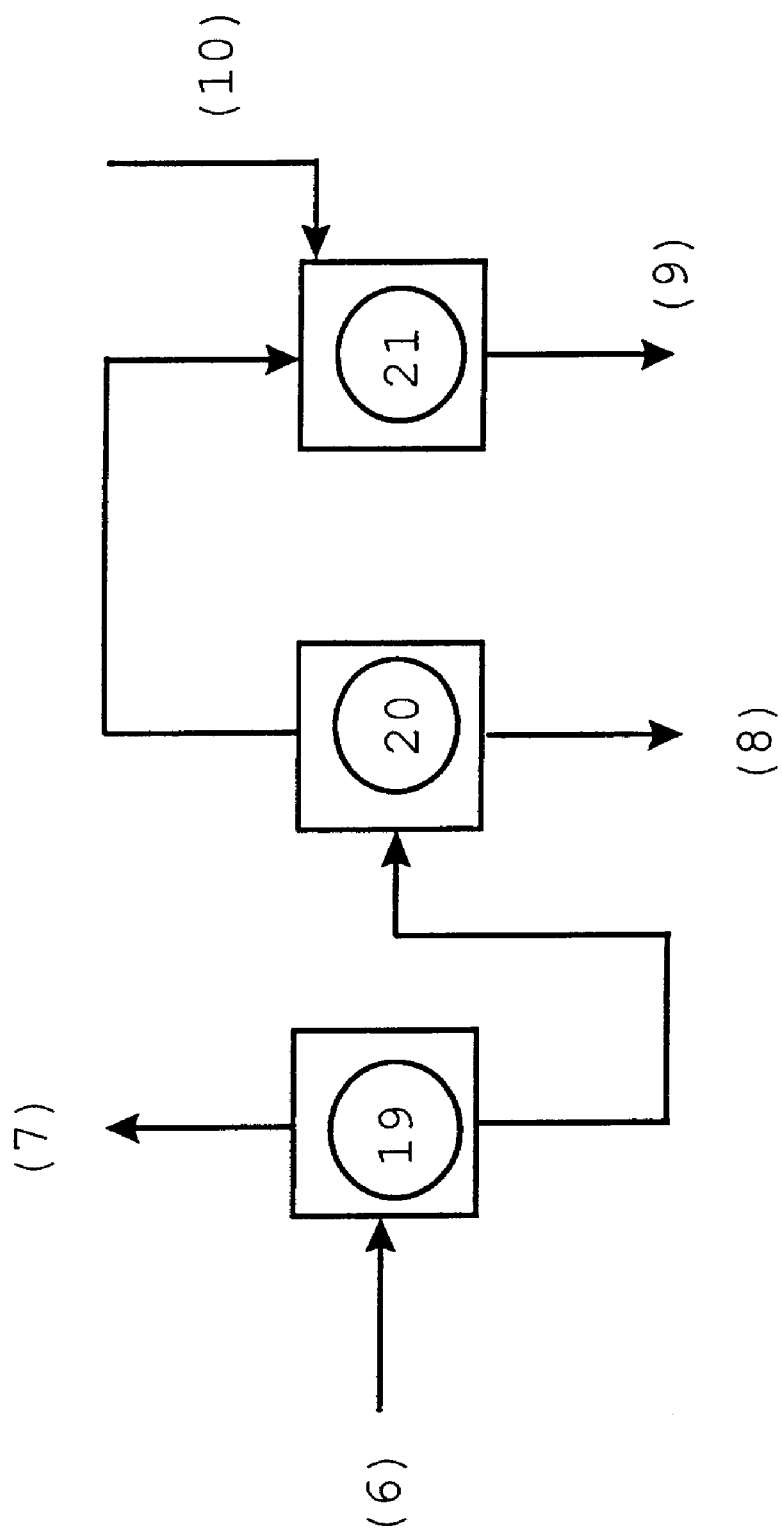

The various embodiments of the process have been shown in the included schematic block diagrams (FIGS. 1, 2 and 3).

In the Figures, the following legend is used:

1 carbon monoxide and hydrogen gas (syngas)
2 ethylenically unsaturated compound
3 catalyst components
4 solvent
5 water
6 crude alcohol
7 light ends
8 heavy ends 9 finished alcohol
10 hydrogen gas
11 one or more gas/liquid reactors
12 one or more gas/liquid separators
13 a centrifuge, coalescer or settler
14 solvent extraction column (catalyst removal)
15 water extraction column (solvent removal)
16 water/solvent distillation column
17 intermediate solvent storage
18 catalyst preparation
19 topping distillation column (light ends)
20 tailing distillation column (heavy ends)
21 hydrofinishing In FIG. 1, the ethylenically unsaturated compound (2), carbon monoxide and hydrogen gas (1) are fed into the reactor(s) (11) that contain(s) catalyst prepared in unit (18). The product is passed to one or more gas/liquid separators (12). Thereafter, the product is send to either of the centrifuge, filterbed coalescer or electrostatic coalescer (13). The solvent layer is recycled together with the catalyst to the reactor(s) (11). The product layer is passed to the solvent extraction column (14), wherein the remaining catalyst is removed. The loaded solvent is passed through conduits A or B to (11) and/or (13). The product is passed to the water extraction column (15), wherein the solvent is removed. The aqueous layer is passed to distillation column (16), to recover water (5) over the top, which is recycled to (15), and to recover solvent (4) at the bottom of (16), which is recycled to storage (17). The conduits to recycle the water and solvent have inlets for water (5) and solvent (4). The product layer (6) that is recovered from (15) may be passed to any suitable work-up train, for instance, such as disclosed in FIG. 3.

FIG. 2 is a representation of a preferred embodiment, wherein the loaded solvent is passed through conduit B to (13). Additionally, this Figure depicts the process wherein part of the crude reaction product is recycled to (11).

Finally, FIG. 3 shows a suitable work-up train, wherein the product (6) is passed to one or more light end distillation columns (9), wherein additionally the residual water is removed, one or more heavy ends distillation columns (10) and finally a hydrofinishing reactor (11). A saponification unit (not shown) before the distillation columns is optional. Besides, the light ends (7) and/or heavy ends (8), after separation from the water (not shown), may be recycled to reactor (11). This is particularly advantageous when a saturated hydrocarbon is added to facilitate the phase separation step.

The invention will be further illustrated by the following examples. In these examples the following abbreviations are used:
BCPE =1,2-bis(cyclooctylenephosphino)ethane
TFSA =trifluoromethanesulphonic acid
NaCl =sodium chloride Reference example A
Hydroformylation has been carried in a 300 ml batch autoclave. The autoclave was filled, under argon atmosphere, with 62 ml $C_{11}$–$Cl_2$ internal linear olefins, 0.63 ml water and 0.755 g n-tridecane (as &C internal standard). Separately, catalyst was prepared in a 100 ml flask, by adding 0.525 g Pd acetate, 1.01 g BCPE, 0.522 g zinc dichloride and 0.92 g TFSA, under argon atmosphere, to 99.0 g anhydrous sulfolane (40° C., stirring), to give a Pd concentration of ca. 400 ppmw and molar catalyst ratios (Pd/BCPE/TFSA/chloride) of 1:1.4:2.6:3.2. One sixth of this catalyst inventory (16.96 g) was added to the batch autoclave. Subsequently also 50 ml 2-ethylhexanol was added. The autoclave was closed, residual air was removed using three cycles of vacuum and syngas pressurizing. Stirring rate was 1000 rpm, using a hollow-shaft stirrer. Then the pressure was set at 56 bar syngas (molar ratio $H_2$/CO of 2.0) and temperature was increased rapidly to 90° C. At the start of the reaction the temperature rose to 105° C. and the pressure dropped. The reaction was maintained at this temperature and at a pressure of 50 bar (using syngas make-up via a constant pressure valve). After 3 h at 105° C., the reactor contents were cooled to ambient temperature. GC analysis indicated that olefin conversion after 3 h was >99.9% and selectivities to alcohol, paraffin and heavy ends were 99.0, 0.5 and 0.5%, respectively (no aldehyde observed).

Reference example B
Part of the product of reference example A was heated to 40° C. (a reasonable model temperature for phase separation in a commercial unit, using tempered cooling water). At this temperature, two liquid phases existed: an upper almost white layer of crude alcohol; and a lower layer of Pd catalyst dissolved in sulfolane (yellow due of presence of Pd catalyst). The layers were separated, sampled, diluted in n-butanol and analyzed by elemental analysis. The data were as follows:

| Layer (g) | Pd (mg/kg) | P (mg/kg) | Cl (mg/kg) | F (mg/kg) |
| --- | --- | --- | --- | --- |
| alcohol 93.2 | 122 | 128 | 224 | 306 |
| sulfolane 4.0 | 4110 | 3288 | 1950 | 2883 |
| partition coefficients | 34 | 26 | 9 | 9 |

Apparently, the Pd catalyst recovery was far from complete. Although for Pd the partitioning coefficient was highest, mass balance indicated that only 59% of the Pd was recovered via the sulfolane layer.

Reference example C
The experiment described under A was repeated using a 40:60 w/w $C_{12}$/$C_{13}$ detergent alcohol, ("DOBANOL" 23, trade mark, linearity ca. 80%), instead of 2-ethyl-hexanol. The molar catalyst ratios (Pd/BCPE/TFSA/Cl) were as follows: 1:1.4:2.0:3.2. Olefin conversion after 2 h and 4 h was 94.6 and >99.9%, respectively. Selectivities after 4 h were 99.5% alcohol, 0.4% paraffin, 0.1% aldehyde (no heavy ends detected). After 4 h reaction time, the product was cooled to 60° C. (still one phase) and split in three nearly equal fractions. These fractions were cooled further to 25, 35 and 45° C., resulting in phase separation in all three cases. After sufficient equilibration time, the layers were separated and samples were taken from both layers and diluted with methanol and analyzed for Pd. The partitioning coefficients for Pd at 25, 35 and 45° C. were 64, 51 and 35, respectively. These data are consistent with the data of example B. Again, Pd catalyst recovery was far from complete and although the distribution improved with decreasing temperature, even around ambient temperature significant amounts of Pd were lost via the alcohol phase. The mass balance at 25° C. indicated that only 85% of the Pd was recovered via the sulfolane layer.

Example 1
To demonstrate the advantages of the invention, an experiment was run in a continuously operating mini-pilotplant consisting of a feed zone, a reactor zone, a first phase separation zone for first catalyst recycling, and an extraction zone for essentially complete recovery and recycling of Pd catalyst and sulfolane.

The feed zone supplied $C_{11}$–$C_{12}$ internal linear olefin (purified over alumina to remove peroxides), $H_2$ (purified over Cu/alumina to remove oxygen), CO (purified over Cu/alumina to remove oxygen and activated carbon to remove carbonyls), BCPE (dissolved in toluene), and water. Before start-up, an inventory of Pd-catalyst (2.7 g Pd, molar ratio Pd/BCPE/TFSA/Cl 1:1.1:2.0:0.43, at a concentration of 3000 ppmw Pd in sulfolane containing 3% w water) was added to the reactor zone. Of the catalyst system only BCPE is made up during the experiment.

The reaction zone consists of two 1.5 liter Inconel-600 Continuous Stirred Tank Reactors (stirrer rate 800 rpm, liquid volume 900 ml each). Reaction conditions were typically 105° C., 70 bar syngas ($H_2$/CO molar ratio 2.0), 150–300 g/h olefin feed, 15%w sulfolane, 1.6 %w water, 300–400 ppmw Pd in reactors, olefin conversion in first and second reactor ca. 86–93% and 97.5–99.5%, respectively. After the second reactor, the reactor product was cooled to 35–40° C. and depressurized to 1.2 bar.

Phase separation started directly but was not complete. The two-phase mixture was subsequently sent down-flow through a small filterbed-coalescer (35–40° C.), consisting of flat stainless-steel filter elements containing fibres increasing gradually in size from 2 mm to 22 mm going from inlet to outlet. The product was fully phase-separated and introduced into a settler, from where the sulfolane phase (containing concentrated Pd catalyst) was recycled back to the reactors and the alcohol phase (still containing significant amounts of diluted Pd catalyst and sulfolane solvent) was transported to a separate alcohol buffer vessel.

In the extraction zone, the alcohol phase was purified in two counter-current liquid/liquid extraction columns (glass, 3 cm diameter, 3.4 m height, stainless steel internals of size 4×4 mm). In the sulfolane extraction column, clean recycle sulfolane was used to remove essentially all Pd residues from the alcohol (phase ratio alcohol/sulfolane ca. 9:1 w/w, temperature 40° C., sulfolane as continuous phase) . In the water extraction column, clean recycle water was used to remove essentially all sulfolane from the alcohol (phase ratio alcohol/water ca. 5:2 w/w, temperature 70° C., water as continuous phase) . The catalyst-loaded sulfolane from the sulfolane extraction column was recycled back to the filter-bed coalescer. The sulfolane-loaded water was fed to a distillation column producing a clean water top product (recycled to water extraction) and a sulfolane bottom product (containing some residual water, ca. 3% w), which was recycled back via a buffer vessel to the sulfolane extraction column. The crude alcohol coming from the mini-pilot-plant was virtually Pd-catalyst- and sulfolane-free.

Typical Pd concentrations during steady-state were: 400 ppmw in reactors, 2600 ppmw in sulfolane recycle, 90 ppmw in crude alcohol product from filterbed coalescer, 900 ppmw in sulfolane bottoms product of sulfolane extraction, 0.2 ppmw in alcohol top product of sulfolane extraction. The other catalyst components roughly behave as the Pd: typical residual levels of phosphorous, TFSA and chloride in the alcohol top product of sulfolane extraction are: 10 ppmw, <5 ppmw and <10 ppmw, respectively. Typical sulfolane concentrations during steady-state were: 15% w in reactors, 8–10% w sulfolane (saturation) in alcohol phases up front of water extraction column, 40 ppmw in alcohol top product of water extraction column.

The run has continued for 732 h and has proven, besides good catalyst retention, also excellent chemical catalyst stability.

Example 2

Model experiments were conducted to determine the efficiency of water extraction to recover sulfolane from representative product alcohols. The starting mixture was composed of "DOBANOL" 23 (trade mark) and sulfolane in ratio 93/7 w/w. To this mixture, 10 or 30%w water was added at four different temperatures (35, 70, 80, 90° C.) . The mixtures were stirred for equilibration and sufficient time was taking for subsequent settling. The resulting two layers (alcohol tops, water bottoms) were separated and analyzed for sulfolane in both layers by GC. The following distribution coefficients were obtained.

| Temperature (° C.) | water fraction added (% w on alcohol/sulfolane) | distribution coefficient of sulfolane (bottoms/top w/w) |
|---|---|---|
| 35 | 10 | 8.3 |
| 35 | 30 | 8.2 |
| 70 | 10 | 7.5 |
| 70 | 30 | 5.9 |
| 80 | 10 | 5.5 |
| 80 | 30 | 5.4 |
| 90 | 10 | 3.7 |
| 90 | 30 | 4.8 |

It is clear that sulfolane preferably goes to the water layer, but that many stages are required to reduce the sulfolane concentration to the desired low levels. Temperature has a negative influence on seperation efficiency.

Example 3

Experiments were carried out to check the effect of additives to improve the Pd distribution coefficient over sulfolane and alcohol phases. For this purpose, batch autoclave experiments were carried out in a 300 ml batch autoclave, as described above under Examples A and C. The autoclave was filled with $C_6$–$C_8$ or $C_{11}$–$C_{12}$ internal linear olefins (I or II respectively), water and n-tridecane (as GC internal standard). Catalyst was prepared using sodium iodide in case of $C_6$–$C_8$ olefins and sodium chloride in case of $C_{11}$–$C_{12}$ olefins (giving a Pd concentration of ca. 400 ppmw and molar catalyst ratio, Pd/BCPE/TFSA/halide, of 1:1.4:2.0:0.4 in anhydrous sulfolane). Subsequently also product alcohol (ca. 40%w) was added. The reaction was carried out at 105° C. and 50 bar. After 2 h at 105° C. and full conversion, the reactor contents were cooled to ambient temperature. Next, the product was mixed with varying amounts of n-heptane (0–50% w) and equilibrated at the selected temperature. Subsequently, both layers were samples and analyzed for Pd concentration using AAS, as follows:

| alcohol derived from (olefin): | I | I | I | II | II |
|---|---|---|---|---|---|
| n-heptane conc. (% w) | 0 | 33 | 50 | 0 | 50 |
| temperature (° C.) | 20 | 20 | 20 | 35 | 35 |
| Pd conc. in top layer (ppmw) | 113 | 23 | 11 | 40 | 12 |
| Pd conc. in bottoms layer (ppmw) | 3320 | 2790 | 2710 | 3320 | 3050 |

-continued

| alcohol derived from (olefin): | I | I | I | II | II |
|---|---|---|---|---|---|
| Pd distribution coefficient (bottoms/top w/w) | 29 | 123 | 255 | 80 | 263 |

It is clear that addition of n-heptane has a beneficial effect on Pd recovery.

Example 4

In order to obtain efficient and fast phase separation, initially a batch centrifuge was used, Subsequently, trials were carried out with a continuous Alfa-Laval LAB 102B-05 centrifuge. This centrifuge was equipped with a so-called purifier-bowl, the type of bowl needed for a liquid-liquid separation, with two liquid outlets. Experiments were carried out with well-mixed feeds of "DOBANOL" 23 (trademark) and Pd-catalyst-containing sulfolane (13.3 %w sulfolane, balance being the alcohol) at a speed of 1500 rpm, 35–50° C., using flows of 125–850 ml/min. In all cases, separation was rapid and complete as could be seen from the absence of any haze (residual sulfolane droplets) as well as the absence of any (Pd-catalyst-related) yellow colour in the alcohol phase.

What is claimed is:

1. A hydroformylation process comprising the steps of:
   (a) contacting one or more ethylenically unsaturated compoundis) in a reaction zone with carbon monoxide and hydrogen gas in the presence of a solvent and a homogeneous catalyst based on a Group 8, 9 or 10 metal, and a non-ionically charged phosphorus ligand to form a crude hydroformylation product;
   (b) allowing a major portion of the solvent, wherein a major portion of the catalyst is dissolved, to separate and be withdrawn from the crude hydroformylation product in a phase separation zone;
   (c) removing from the separated hydroformylation product emerging from step (b) substantially all remaining catalyst dissolved therein with a non-aqueous extractant in an extraction zone.

2. A hydroformylation process according to claim 1, wherein the non-aqueous extractant used in step (c) is the same substance as the solvent used in step (a).

3. A hydroformylation process according to claim 2, wherein the amount of extractant used in step (c) is between 0.9 and 1.1 times the amount of solvent that is dissolved in the hydroformylation product.

4. A hydroformylation process according to claims 1 or 2, wherein the following step is added:
   (d) removing from the extracted hydroformylation product emerging from step (c) substantially all remaining solvent and/or extractant dissolved therein with a washing medium, in a washing zone, separating the solvent and/or extractant from the washing medium emerging from the washing zone and optionally reusing each.

5. A hydroformylation process according to claims 1 or 2, wherein the extraction of step (c) is conducted in a column equipped with a rotating disk contactor or a packed bed column.

6. A hydroformylation process according to claims 1 or 2 wherein in step (b) the crude hydroformylation product is cooled to a temperature within the range of 0 to 50° C.

7. A hydroformylation process according to claims 1 or 2, wherein the phase separation of step (b) is assisted by the use of a centrifuge, a filterbed coalescer or an electrostatic coalescer.

8. A hydroformylation process as claimed in claims 1 or 2, wherein liquid saturated hydrocarbons are fed to the phase separation zone of step (b).

9. A hydroformylation process according to claims 1 or 2, wherein a portion of the hydroformylation product emerging from step (b) is recycled to the reaction zone.

10. A hydroformylation process according to claims 1 or 2, wherein the solvent is a sulphone, a compound having 2 or more cyano groups, or a mixture comprising the sulphone and/or the compound having 2 or more cyano groups together with a protic solvent; the ethylenically unsaturated compound is an olefin or a mixture of olefins having from 4 to 24 carbon atoms per molecule, the carbon monoxide and hydrogen gas are supplied in a ratio within 5:1 to 1:5, and wherein the hydro-formylation process is carried out at a temperature in the range of 50 to 200° C. and at a pressure in the range of 1 to 300 bar absolute.

11. A hydroformylation process as claimed in claim 4, wherein the washing medium consists essentially of water.

* * * * *